United States Patent [19]

Keyworth et al.

[11] Patent Number: 4,570,026

[45] Date of Patent: Feb. 11, 1986

[54] PRODUCTION OF ISOBUTENE FROM METHYL TERTIARY BUTYL ETHER

[75] Inventors: Donald A. Keyworth, Houston; Cecil G. McFarland, League City, both of Tex.

[73] Assignee: Petro-Tex Chemical Corporation, Houston, Tex.

[21] Appl. No.: 522,603

[22] Filed: Aug. 12, 1983

[51] Int. Cl.[4] .......... C07C 1/00; C07C 7/00; C07C 7/12; C07C 4/08

[52] U.S. Cl. .............. 585/312; 585/639; 585/324; 585/327; 585/641; 585/649; 585/811; 585/856; 585/864

[58] Field of Search .......... 585/639, 324, 327, 312, 585/641, 642, 649, 811, 856, 824, 864, 866

[56] References Cited

U.S. PATENT DOCUMENTS

| | | | |
|---|---|---|---|
| 4,232,177 | 11/1980 | Smith | 585/324 |
| 4,320,232 | 3/1982 | Volkamer et al. | 585/639 |
| 4,398,051 | 8/1983 | Araki et al. | 585/639 |
| 4,409,421 | 10/1983 | Herwig et al. | 585/324 |

FOREIGN PATENT DOCUMENTS

| | | | |
|---|---|---|---|
| 54805 | 6/1982 | European Pat. Off. | 585/639 |
| 2096604 | 10/1982 | European Pat. Off. | 585/639 |
| 1176620 | 7/1968 | United Kingdom | 585/324 |

*Primary Examiner*—D. E. Gantz
*Assistant Examiner*—Chung K. Pak
*Attorney, Agent, or Firm*—Kenneth H. Johnson

[57] ABSTRACT

MTBE can be dissociated with high selectivity to isobutene and methanol over acid action exchange resin catalysts using very high LHSV, e.g. of 7 to 35 at pressure drops of 0.5 to 50 psig through the fixed bed at reaction pressure of 0.5 to 4 atmospheres and bed temperatures in a fixed bed tubular-reactor in the range of 90° C. to 160° C. Good conversions are obtained and undissociated MTBE and by-products of the dissociation may be recycled to a liquid phase MTBE synthesis.

22 Claims, 6 Drawing Figures

PRODUCTION OF ISOBUTENE FROM METHYL TERTIARY BUTYL ETHER

BACKGROUND OF THE INVENTION

1. Field of the Invention

The present invention relates to a process for the dissociation of methyl tertiary butyl ether (MTBE) to produce isobutene.

2. Related Art

The reaction to produce MTBE is known to be reversible, i.e., the MTBE will dissociate to produce methanol and isobutene which were originally combined to produce the MTBE. For example, U.S. Pat. Nos. 3,121,124; 3,170,000; 3,634,534; 3,634,535; 4,232,177 and 4,320,232 disclose the dissociation alkyl-tertiary alkyl ethers using ion exchange resin catalysts.

MTBE is of economic importance because of its use as an octane improver in unleaded gasoline. However, there may be a time when MTBE will be in over capacity or its cost very low because of large numbers of producers. One interesting aspect of MTBE production is the selective nature of the reaction of methanol with the isobutene as compared to the other components in a $C_4$ stream. That is, the isobutene may be substantially removed from a $C_4$ stream by contacting the stream with methanol in the presence of a suitable acid catalyst (most processes use acidic cation exchange resins). The separation of the MTBE from the unreacted components of the $C_4$ stream is easily effected by distillation and a high purity MTBE product is produced.

Hence the dissociation of MTBE will produce a stream containing substantially only isobutene, as the olefin, methanol; and some oxygenated compounds and polymer impurities. The dissociation of MTBE using a suitable catalyst is a relatively clean process for obtaining an isobutene stream, compared to the cold acid treatment by which high purity isobutene is currently obtained. Thus, with the increasing demand for isobutene, the dissociation of MTBE for isobutene is viable and economic. Furthermore, the cold acid process not only requires large amounts of energy, but is highly corrosive because of the sulfuric acid used. The use of cationic resin catalysts or other catalyst such as phosphoric acid supported on silica gel, alumina, supported metal sulfates for the dissociation require less energy and are substantially free of corrosion.

The dissociation reaction is favored by higher temperatures than the reaction of methanol and isobutene. The former reaction is endothermic, whereas the latter reaction is exothermic. The acid cation exchange resins are somewhat more active than other catalyst, hence somewhat lower temperatures are required for the dissociation, thus less energy input is required and operation at lower pressures is possible. Those acidic cation exchange resins used heretofore have initially exhibited good selectivities and conversion, however, as the reaction continues and higher temperatures are required to obtain the optimum results, degradation of these catalysts results. The degradation has been both physical, e.g., melting, and chemical, e.g., loss of the sulfuric groups which are incorporated in these resins to form acid sites. Furthermore, operating a system to maximize the dissociation of the MTBE, when the catalyst is rapidly degrading, requires greater energy, higher temperatures and loss in selectivity to isobutene.

The use of acid cation exchange resins in the past for the dissociation of methyl tertiary butyl ether has been demonstrated, i.e., U.S. Pat. No. 3,121,124 (Verdol) using a gel type catalyst (Dowex 50) and U.S. Pat. No. 4,232,177 (Smith) used a macroreticular catalyst (Amberlyst 15) in a process designated as catalytic distillation.

Both of these catalysts exhibit instability at the higher temperatures required for dissociation, i.e., the sulfonic groups are lost from the resin. This effect becomes more pronounced and accelerated with the increases in temperature which are required as the catalysts age. Moreover, the dissociation of the ether is an endothermic reaction which is favored by the absence of a liquid phase, that is, an entirely vapor process such as Verdol used is preferred for the dissociation as compared to the Smith process which is partially in the liquid phase because of the nature of distillation, i.e., a distillation contains both vapor phase (the distillate) and a liquid phase (the internal downflow).

Since the vapor phase favors the dissociation reaction, many dissociation processes employ catalyst which can operate at higher temperatures without damage, however, these catalysts would appear not to be as selective as the cation exchange resin catalysts, nor quite as active. Also since the reaction is endothermic, catalysts which operate at higher temperatures require a greater input of energy into the system, which on an industrial scale may make them uneconomic.

It has been found that stablized cation exchange resins, i.e., stabilized and designed to operate at higher temperatures, actually are more active at lower temperatures than prior unstable catalysts and the thermal stability of the catalyst in use exhibit a favorable time trend.

It is an advantage of the present invention that high selectivity to isobutene production is obtained at reasonable conversion rates, using moderate temperatures. It is a feature of this invention that the unconverted MTBE may be recycled to the reaction for the synthesis of MTBE.

SUMMARY OF THE INVENTION

Briefly the present invention is a process for producing high purity isobutene by the dissociation of MTBE in vapor state in a fixed bed of macroreticular acid cation exchange resin, preferably a thermally stabilized resin, at a bed temperature in the range of 90° C. to 160° C., preferably 120° C. to 150° C., said MTBE vapor (stream containing MTBE vapor) being at an inlet temperature of 110° C. to 150° C., preferably 115° C. to 145° C. at an LHSV (liquid hourly space velocity) of 7 to 35, preferably from from 10 to 30 and more preferably from 14 to 25 (corresponds to 11.4 to 57, 16.3 to 48.9, and 26.5 to 40.8 weight hourly space velocity, respectively), at a pressure drop through said fixed bed in the range of 0.5 to 50 psig and at a reaction pressure in the range of 0.5 to 4 atmospheres, whereby a portion of the MTBE is dissociated to methanol and isobutene.

In a particular embodiment of the present invention the process comprises producing MTBE by reacting methanol and isobutene contained in a hydrocarbon feed in liquid phase in a first fixed bed reactor, vaporizing a portion of the MTBE produced and feeding the vaporized MTBE to a second fixed bed reactor for the dissociation reaction described, separating undissociated MTBE from isobutene and recycling the undissociated MTBE to the first reactor.

The unreacted MTBE and dissociated isobutene from the second reactor may be separated by distillation whereby the MTBE is recovered as a bottoms and the isobutene is the overhead. The major amount of methanol and by-product heavy materials are also carried off in the bottoms. The by-products comprise oligomers of isobutene and tertiary butyl alcohol. In addition, the bottoms may contain some isobutene. The bottoms are recycled to MTBE synthesis in the first or second reactor in a multiple reactor system. As an additional step, the isobutene which contains some methanol (azeotrope) may be taken to a wash column where the methanol is removed by washing with water. By this means substantially all of the methanol is removed from the isobutene which is now a very high purity product. The wash water may be fractionated to recover methanol for recycle to the MTBE reactor.

In the two step embodiment the recycle of the undissociated MTBE to the MTBE reactor is an important feature of the present invention. The residual MTBE after the dissociation, is not an acceptable product, that is, it contains methanol, isobutene and some oligomers. Furthermore, this MTBE containing stream is not an acceptable recycle to the dissociation reactor, as such, because the by-product would build up and ultimately shut the process down.

However, by recycling the MTBE bottoms stream to the MTBE reactor the impurities are removed in the usual manner in that reactor, i.e., methanol and isobutene are reactants to produce MTBE. Furthermore, the oligomer by-product in MTBE bottoms from the dissociation is primarily diisobutene, which can be tolerated in MTBE employed as an octane improver in motor fuels up to about 2%. At the lower temperatures used to carry out the synthesis, recycle MTBE is not subject to a great deal of dissociation, which is nonetheless limited by the reversibility of the reaction. Further, the MTBE in the recycle will act as a diluent to reduce the heat of reaction in the MTBE synthesis and because of some degree of dissociation may provide an intrareaction heat sink. The MTBE synthesis per se is not a part of the present invention other than in the combination recited and any of those fixed bed, liquid phase methods disclosed (particularly the commercialized processes) may be employed in the first reactor.

Another aspect of the invention is the use of the thermally stabilized cation exchange resin as the dissociation catalyst. Their selectivity and conversion are superior to other types of cation exchange resins under the same conditions of temperature, pressure and residence time. Their greater activity actually allows for operation well below the high temperatures for which they were designed. In addition to this benefit a further benefit arises when, in the normal course of events the catalyst activity declines, the operating temperatures can be increased and the catalyst life thereby extended longer than unstabilized resin catalysts.

The term "thermally stabilized" means an acid cation exchange resin which has been treated or modified to have greater resistance to degradation by temperature, both as to duration and magnitude of temperature, than the untreated or unmodified resin, by the incorporation of electron withdrawing groups, such as halogens therein, that is, the electron withdrawing groups are attached to the resin, by having—$SO_3$ groups attached at the para position to the divinyl benzene and ethylstyrene units or combinations of the two.

The term liquid hourly space velocity (LHSV) means the liquid volumes of total material fed per volume of reactor containing catalyst, per hour.

DETAILED DESCRIPTION OF THE INVENTION

Figure 1:
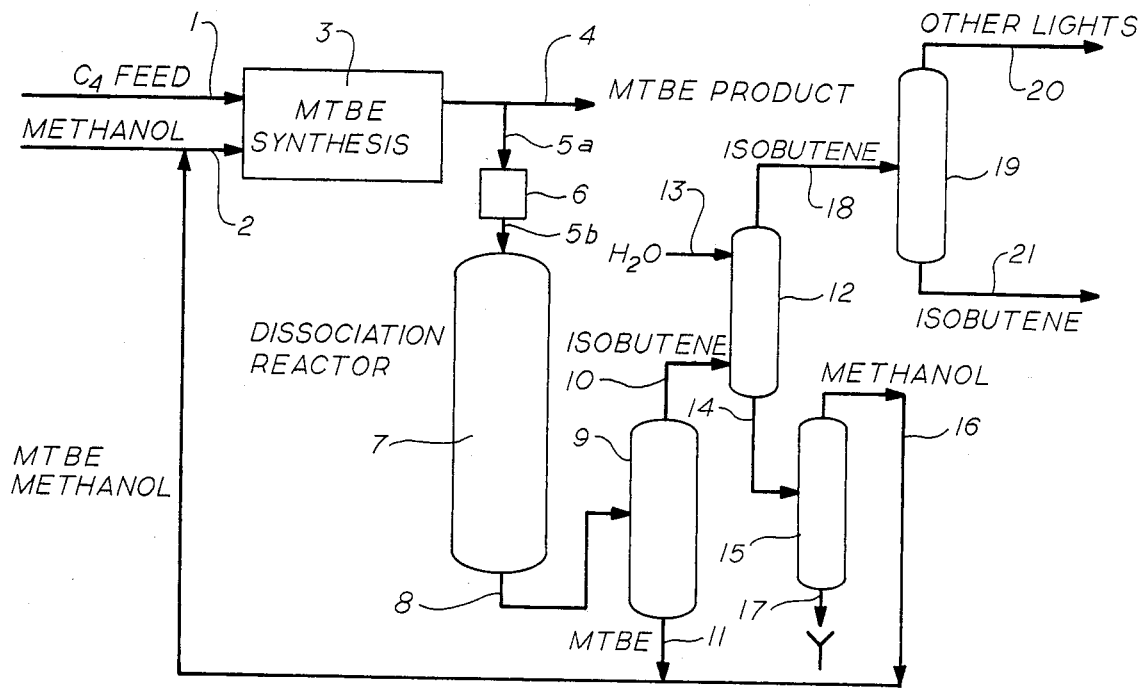
FIG. 1 is a schematic depiction of an embodiment of an integrated system for carrying out the present process.

In order to produce high purity isobutene from the dissociation of MTBE, the feed to the dissociation reaction must be a high purity material itself. Thus the MTBE feed is 95% by weight or greater MTBE. The remainder of the feed is isobutene, oligomers (mainly dimer) and some normal $C_4$. Preferably the MTBE is greater than 97% by weight of the vaporized feed going to the dissociation reactor.

It has been found that high LHSV; i.e., 7 to 35 preferably over 10 to 30 increases selectivity to isobutene at a given temperature. Stated otherwise at a given LHSV, an increase in the inlet temperature of the feed reduces the selectivity to isobutene. At these feed rates it is difficult to heat the catalyst bed sufficiently to maintain the endothermic reaction. Thus the present reactor is preferably a tubular type reactor with an appropriate heat exchange medium, supplying heat to the catalyst tubes. At these very high rates of feed, even in a one inch tubular reactor, the heat exchange from the heat exchange medium is not adequate to maintain the reaction and the feed must be heated. It should be appreciated at a given LHSV in the ranges recited herein, a high inlet temperature for the feed, although reducing selectivity, does increase the conversion of MTBE. Hence, within the temperature ranges and LHSV ranges recited herein, one should optimize the conditions to obtain the desired result. That is, a few degrees of increase of the inlet temperature may produce only a slight drop in selectivity and a more than offsetting increase in conversion, which would result in a higher yield of isobutene (yield=conversion×selectivity).

The high LHSV's are particularly advantageous in that the production of isobutene oligomers (principally dimers) is reduced as is the production of dimethyl ether (DME). The low oligomers production is advantageous in the recycle of undissociated MTBE, since as noted above there is a limit on the amount of oligomer acceptable in the MTBE utilized as an octane improver. The low DME production is an advantage, since only low amounts e.g. 50 ppm DME are acceptable in isobutene. Hence, the less DME in the isobutene stream, the easier the subsequent separation by distillation. (The DME is more volatile than isobutene, hence all of the DME present will go with the isobutene in the distillation of the product from the dissociation reactor.)

Thus, it would appear that higher feed temperatures would be beneficial to the dissociation reaction within the useful temperature range of the catalyst, however, higher feed temperatures, not only favor the dissociation, but also favor the oligomerization of the isobutene with a loss of selectivity to isobutene. Preferably the temperature of vaporized feed is from about 110° C. to 150° C. more preferably 115° C. to 145° C. with the total heat imput to the dissociation being such to provide the bed temperatures set out above.

As noted, the undesirable oligomerization is favored with increased temperature. However, by increasing the LHSV within the specified ranges the oligomerization is reduced. The increased temperature also favors the conversion. Hence at high through puts (high LHSV), high conversions and high selectivity are obtained with a favorable unit productivity.

The optization of the operation of the dissociation reactor within the ranges provided and the guidelines provided here and in the examples is merely routine. The variables for a given feed are the inlet temperature, LHSV and bed temperature (the temperature of the heat exchange medium surrounding the reactor tube being adjusted to make up the bed temperature). The temperature in the catalyst bed is controlled by the heat input from heated feed vapors (sensible heat) and the heat exchange medium.

The dissociation reactor is an important aspect of the reaction, since a large amount of heat must be supplied to the reactor to carryout the endothermic dissociation. A tubular reactor is preferred since heat can be supplied by both the heated vaporized feed and heat exchange medium surrounding the reactor tube. Generally, a plurality of tubes of ⅛ to 2 inches outside diameter are mounted in a shell. The resin catalyst is loaded in the tubes and heat exchange medium at the desired temperature passes through the shell and around the tubes. The tubes may be of larger diameter, which will be limited by the efficiency of heat transfer into the bed. The tube length can vary greatly, e.g., 2.5 to 12 feet, with the desired LHSV being a consideration of tube size also.

The cation exchange resin catalysts available have been investigated for the present invention. The gel type sulfonated styrene-divinyl benzene copolymer as disclosed in U.S. Pat. No. 3,121,124 to Verdol, discussed earlier, were found to be very poor for MTBE dissociation.

The catalysts useful for the present invention are in the macroreticular form which has surface areas of from 20 to 600 square meters per gram. Catalysts suitable for the present process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly, suitable polymers which contain sulfonic acid groups and are copolymers of aromatic monovinyl compounds with aromatic polyvinyl compounds, particularly divinyl compounds, in which the polyvinyl benzene content is preferably 1 to 20% by weight of the copolymer (see, for example, German Patent Specification No. 908,247).

The preferred catalyst is one which is thermally stabilized. Varying degrees of stabilization have been obtained by the incorporation of electron withdrawing groups, particularly halogens, such as bromine and chlorine into the resin polymer. U.S. Pat. Nos. 3,256,250; 3,342,755; 4,269,943 and British Pat. No. 1,393,594 describe several such procedures.

A preferred stabilized catalyst of this type is that described in U.S. Pat. No. 4,269,943, wherein chlorine or bromine are added to the polymer prior to sulfonation. In this manner the halogen is attached to the aromatic nuclei of the resin polymer. A particularly preferred form of this catalyst is the chlorine stabilized catalyst.

The thermal stability may also be obtained by attachment of —$SO_3H$ groups at the para position to the divinyl benzene and ethylstyrene units (the ethyl and/or vinyl groups being attached in the meta positon relative to each other). This is discussed in an article by Leonardus Petrus, Elze J. Stamhuls and Geert E. J. Joosten, "Thermal Deactivation of Strong-Acid Ion-Exchange Resins in Water", Ind. Eng. Chem. Prod. Res. Dev. 1981, 20, pages 366–377.

The ion exchange resin is preferably used in a granular size of about 0.25 to 2 mm, although particles from 0.15 mm up to about 2 mm may be employed. The finer catalysts provide high surface area, but also result in high pressure drops through the reactor. The increased pressure drop as a result of the smaller granular size, may be offset by using shorter reactor tubes, i.e., from about 2 to 4 ft. long. However, catalyst particles of the preferred size and substantially free of fines are not subject to the large pressure drops. The preferred granular size is 15 to 40 mesh (approximately 0.420 to 1.3 mm), which is substantially free of fines. Even at the very high LHSV's of the present invention the preferred granular size can be used in longer tubes, i.e., six to seven feet without excessive pressure drops, i.e., less than 50 psig.

The very high LHSV's used herein require a large input of heat to maintain this reaction. As described this heat of reaction is supplied by the heated vapors and the heat exchange medium (by indirect heating of the catalyst bed). If the incoming vapors are heated to too high a temperature, a substantial amount of dimerization of the isobutene occurs with a corresponding drop in isobutene selectivity. However, the desirable high LHSV's require a sufficient input of heat to maintain the dissociation. Thus a major portion of the heat of reaction must be supplied by the heat exchange medium. The heat exchange medium may enter the tubular reactor at 120° C.–160° C. or more and contact the tubes containing the catalyst at high temperature. Thus the catalyst adjacent to the tube walls may be subject to very high temperatures, even though the temperature drop to the center of the tube bed may be as much as 35° C. Hence, it can be appreciated that ability of the catalysts to withstand thermal degradation will be an important consideration initially and also over the life of the catalyst where some increase in the bed temperature can be expected to compensate for the inevitable loss of sulfonic groups or other factors which will result in a decline in catalyst activity.

The life of the catalyst can also be adversely affected by catalyst poisons. The feed to the reactor should be free of any poisons, which include cations, particularly metals, and amines.

Referring to FIG. 1 a schematic representation of the complete system for producing high purity isobutene from a $C_4$ stream containing 5 to 40 weight % isobutene, the remainder being isobutene, n-butene, n-butane and trace amounts of $C_3$ and $C_5$ hydrocarbons.

The $C_4$ feed 1 and methanol 2 are fed to the reactor as known in the art for the liquid phase preferential reaction of isobutene and methanol to form MTBE. Presently there are various liquid phase systems producing MTBE commercially. All are believed to be fixed bed acid cation exchange resin. The reaction is exothermic, generally conducted at 90°–120° C. A reactor or series of reactors as described below for the dissociation is a satisfactory means for carrying out this reaction. In addition to the reactor there may be associated water wash towers (not shown) to remove methanol from the unreacted materials of the feedstream, methanol recovery systems (not shown) and the like, which (other than the fact a fixed bed resin system is used for the liquid phase synthesis of MTBE) form no part of the present invention and are indicated as 3.

Figure 3:
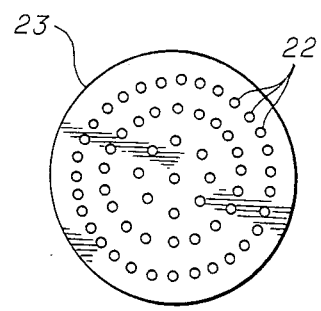
FIG. 3 is a cross sectional view of the reactor of FIG. 2 taken along line 3—3.
Figure 2:
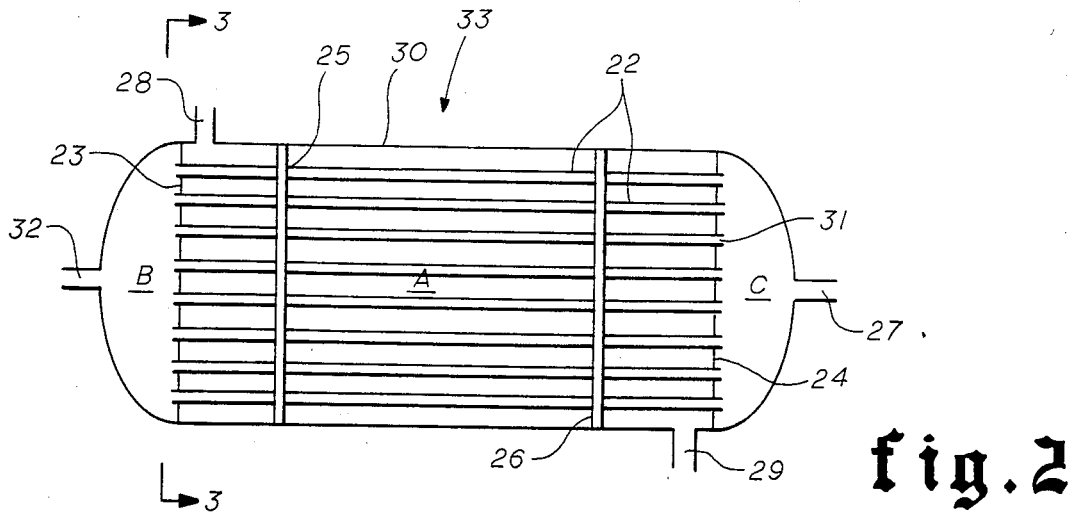
FIG. 2 is a cross sectional elevation of a reactor for carrying out the dissociation process of the present invention.
Figure 4:
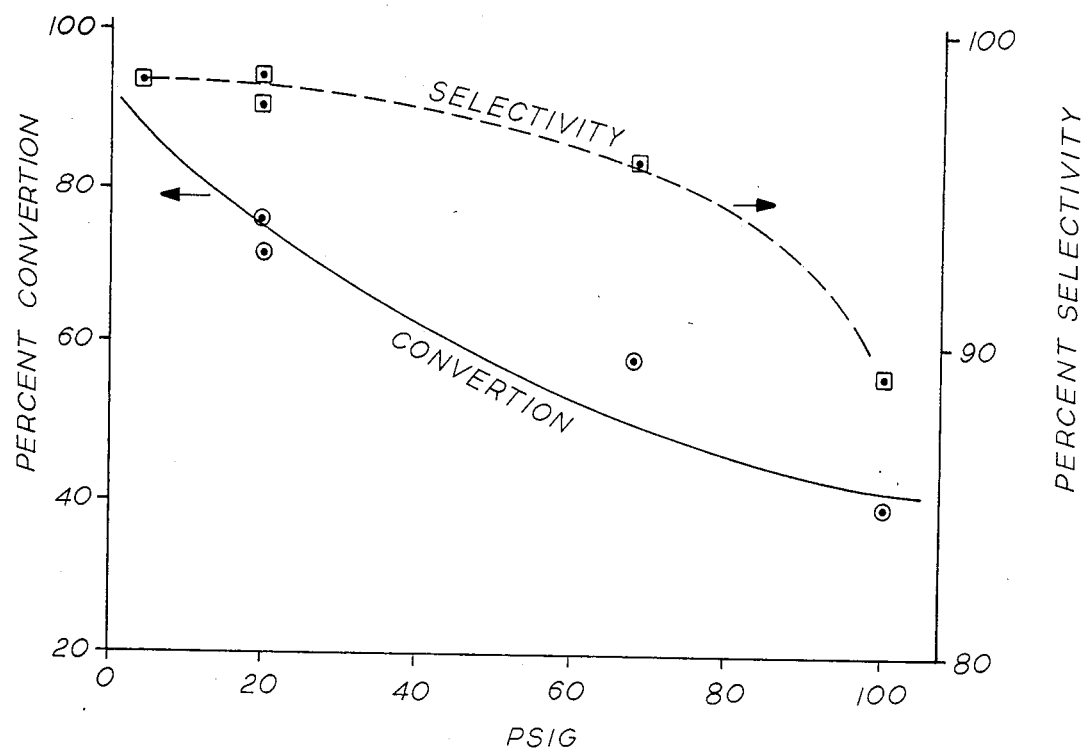
FIG. 4 is a graphic representation of the effect of operating pressure in MTBE conversion and isobutene selectivity.
Figure 5:
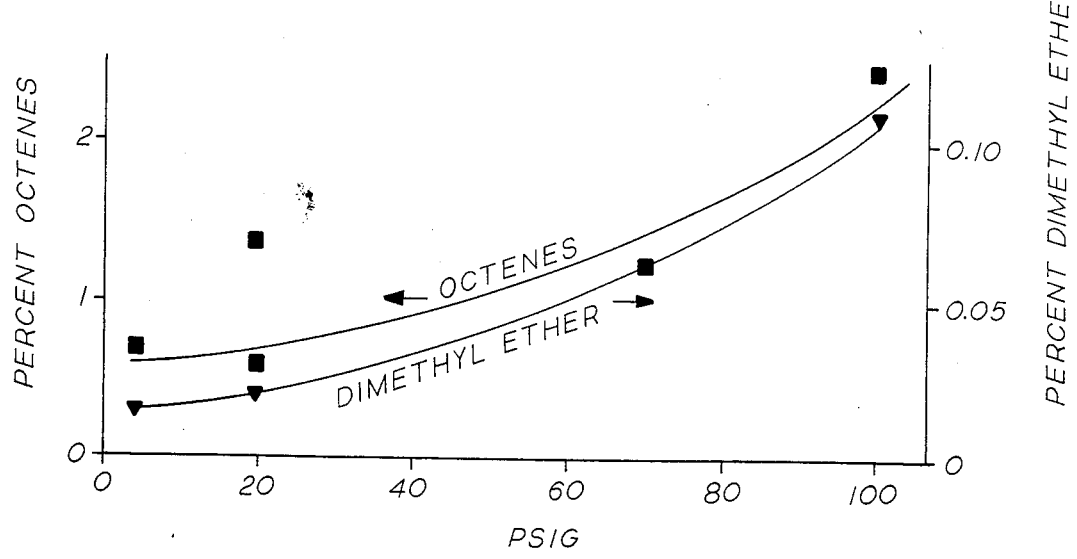
FIG. 5 is a graphic representation of the effect of operating pressure on by-product production.

A portion 4 of the MTBE produced may be recovered for sale. Another portion 5a is passed to a vaporizer 6 where it is vaporized and preheated prior to entry as vaporized MTBE stream 5b into reactor 7. The reactor 7 is preferably of a tubular configuration as shown in FIGS. 2 and 3. A downflow configuration of the reactor works quite well for the present dissociation. The conditions and mode of operation are those set forth elsewhere herein. Typically a conversion of the MTBE between 60 and 80 weight percent can be obtained at the high LHSV's and temperatures described, with selectivity of over 90% to isobutene. The dissociated material 8 leaves the reactor and goes to a splitter where the isobutene and some methanol are removed as overhead 10 and most of the methanol, isobutene oligomer, dimethyl ether and undissociated MTBE are recovered as bottoms 11 and recycled to the MTBE synthesis 3, conveniently with the methanol feed 2.

The overhead isobutene 10 passes to a wash tower 12 where it is contacted with water 13. Any methanol entrained or azeotroped with the isobutene is dissolved in the water 14 and removed to distillation column 15 where the recovered methanol is distilled and desirably recycled via 16 to the MTBE synthesis 3. The wsh water 17 is disposed of to an appropriate treatment pond (not shown).

The methanol free isobutene 18 is subjected to a further distillation in tower 19 where DME and other lights 20 are removed and high purity (98+%) isobutene is the recovered bottoms 21.

The heat exchange fluid is in indirect contact with the fixed catalyst bed. FIG. 2 shows a conventional and preferred means of obtaining this contact. Reactor 33 is a multitube reactor comprising a shell 30 having mounted therein tubes 22, usually of ⅛ to 2 inches outside diameter. The reactor is shown horizontally, however, it could be vertical or inclined. The tubes 22 are mounted through plates 25 and 26 which are to prevent fluid communication between the coolant area A, which is adjacent to the tubes, and the feed entry area B and product exit area C. The tubes 22 are in fluid communication with areas B and C. A feed entry pipe 32 is located in the B area and a product exit pipe 27 is located in the C area. Heat exchange medium is provided into the A area via pipe 29.

The tubes 22 are packed with the cation exchange resin in granular form 31 and means such as screens (not shown) are fitted to each tube to retain the catalyst therein. FIG. 3 shows an arrangement of tubes 22 in header plate 23.

The dissociation reaction is endothermic and the heat exchange medium, e.g., steam, silicon fluids and the like, provides the means for maintaining the reaction temperature in the catalyst bed, in conjunction with the heated MTBE stream coming into the reactor.

The following examples are presented to illustrate the invention and are not intended to limit its scope. The olefin product analyses were obtained by gas chromatography of the hydrogenated olefins. In the examples the term "yield" means conversion X selectivity. In the present examples conversion means conversion of MTBE, and selectivity refers to the product indicated. Also the term STY appears in the examples, this means space times yield of isobutene and is equal to LHSV X selectivity to isobutene X conversion X 100. This term provides a measure of the productivity of the unit in question for the production of the isobutene under the conditions given. It allows for a comparison of the results obtained in the reactor under the different conditions employed.

EXAMPLE 1

Figure 6:
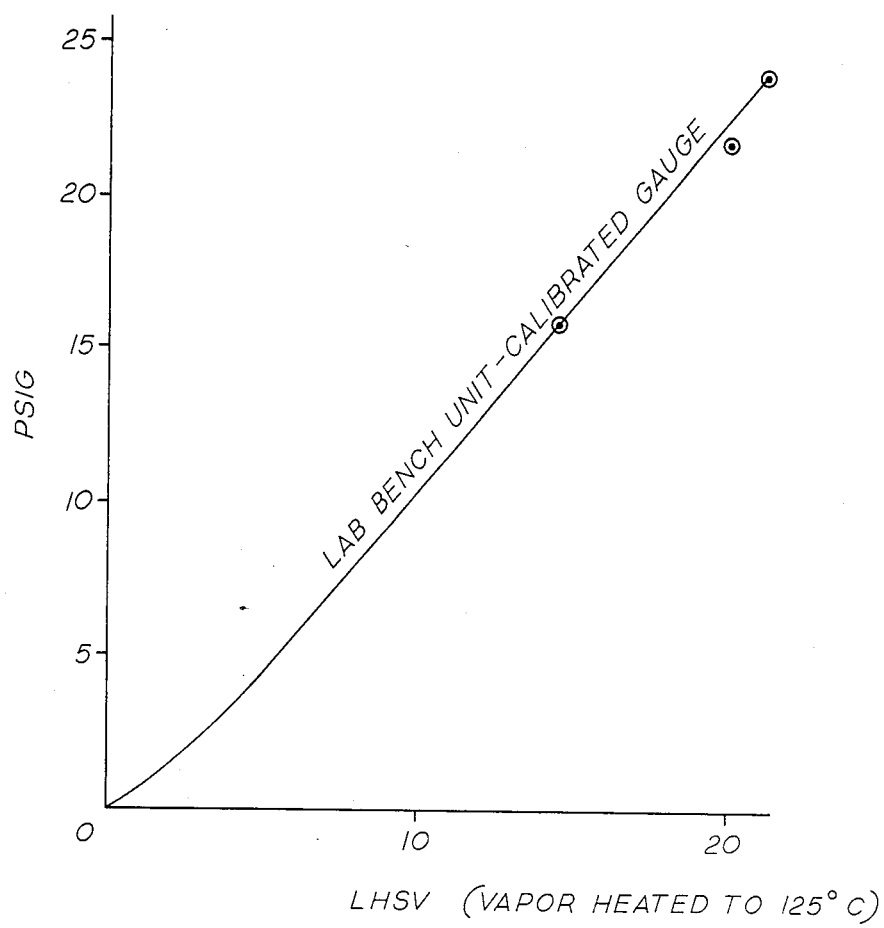
FIG. 6 is a graphic representation of the pressure drop (P) in the experimental reactor the through fixed bed at various LHSV's.

In these examples MTBE was passed over Dow MSC-1, which is a macroreticular resin of sulfonated copolymers of styrene and divinyl benzene being in the form of beads of 20–50 mesh size. The reactor used was a jacketed stainless steel tube, having a ½" OD (0.065" wall thickness) 48 inches long. Thirty-four inches (75 cc) of the "wet" (water) catalyst was loaded into the tube. The catalyst shrinks to 30 inches when the water is displaced. Above the catalyst was an 8 inch bed of glass beads. The reactor was heated by silicone oil introduced into the jacket. The feed to the reactor was vaporized and preheated in a jacketed tube heated by silicone oil prior to entry into the reactor, which was vertical with feed passing downward, first contacting the glass beads. The reactor was operated at atmospheric pressure at various LHSV's and inlet temperatures for the feed and silicone oil. In TABLE I the temperature of the silicone oil going into the jacket for both the vaporizer and the reactor is reported. These conditions are reported in TABLE I as well as the temperature along the catalyst bed (three points). The results of the dissolution are set out in TABLE II. The feed was a high purity MTBE (99.9+%). The conversion is based on MTBE. The pressure drop through the reactor can be determined at each LHSV by reference to FIG. 6 which shows the Δ P(i.e., Outlet gauge pressure—inlet gauge pressure) for MTBE vapor at 125° C. over the range of LHSV used. The 19 runs represent a continuous run over a seven day period with the LHSV being increased as the run continued. The reaction was at atmospheric pressure, that is, no back pressure was applied to the outlet although there was a pressure drop through the system.

In TABLE II the analyses of samples taken during the run are reported. Various samples were taken during the run under each set of conditions and the degree of consistency of the data is reported with the present analyses of the product leaving the reactor.

EXAMPLE 2

In another set of runs using the same reactor, catalyst and feeds, the effect of pressure in the reaction, i.e., reaction pressure, had on the operation of the process at various LHSV and temperatures were evaluated. The conditions including the reactor profile (recorded bed temperature at three points) are set out in TABLE III. The results of each run are set out in TABLE IV.

TABLE I

| | RUN NO. | | | | | | | | | | | | | | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| LHSV | 7 | 7 | 7 | 7 | 7 | 10 | 10 | 11.8 | 14.3 | 14.3 | 18.4 | 18.4 | 20.0 | 20.0 | 20.0 | 20.0 | 20.4 | 20.0 | 20.0 |
| MTBE Preheater Inlet °C. | 110 | 118 | 122 | 123 | 135 | 132 | 130 | 130 | 130 | 130 | 133 | 125 | 114 | 140 | 128 | 142 | 122 | 145 | 121 |
| Bath In (Reactor) °C. | 110 | 118 | 122 | 123 | 130 | 123 | 130 | 130 | 130 | 131 | 137 | 137 | 130 | 130 | 130 | 139 | 141 | 148 | 150 |
| Reactor Profile (Catalyst) (INCHES) | | | | | | | | | | | | | | | | | | | |
| 0 | 80 | 80 | 93 | 85 | 85 | 95 | 100 | 101 | 101 | 105 | 106 | 107 | 107 | 111 | 109 | 116 | 110 | 120 | 115 |
| 14 | 77 | 82 | 72 | 75 | 77 | 69 | 73 | 73 | 73 | 75 | 78 | 75 | 73 | 72 | 72 | 72 | 72 | 73 | 74 |
| 30 (bottom) | 97 | 113 | 101 | 104 | 111 | 94 | 100 | 95 | 93 | 96 | 100 | 92 | 90 | 87 | 87 | 91 | 92 | 94 | 97 |
| % C (MTBE) | 71.2 | 79.1 | 81.0 | 83.7 | 91.1 | 73.0 | 79.3 | 75.3 | 67.6 | 68.3 | 73.8 | 62.8 | 53.0 | 54.9 | 56.1 | 58.9 | 61.3 | 67.2 | 68.1 |

TABLE II

| | EXAMPLE | | | | | | | | | |
|---|---|---|---|---|---|---|---|---|---|---|
| | 1 | 2 | 3 | 4 | 5 | 6 | 7 | 8 | 9 | 10 |
| Methyl Ether, Wt. % | .059 | .117 | .102 | — | .317 | .040 | .056 | .038 | .021 | .038 |
| Isobutylene, Wt. % | 45.03 | 45.27 | 45.43 | — | 50.99 | 44.15 | 45.51 | 45.60 | 41.68 | 44.32 |
| MTBE, Wt. % | 28.78 | 20.87 | 18.94 | — | 8.98 | 27.05 | 20.73 | 24.73 | 32.41 | 26.20 |
| Methanol, Wt. % | 23.13 | 27.97 | 31.35 | — | 26.08 | 27.31 | 31.33 | 28.30 | 25.10 | 27.95 |
| TBA, Wt. % | .065 | .045 | .053 | — | .049 | .039 | .033 | .040 | .043 | .040 |
| Octenes, Wt. % | 2.179 | 4.798 | 3.786 | — | 10.93 | 1.376 | 2.079 | 1.250 | .742 | 1.441 |
| Dodecenes, Wt. % | .757 | .832 | .356 | — | 2.659 | .063 | .297 | .054 | .035 | .043 |
| Data Consistency | .846 | .965 | 1.111 | — | .719 | 1.050 | 1.148 | 1.057 | 1.036 | 1.07 |
| Conversion (isobutene) | .724 | .793 | .805 | — | .919 | .726 | 784 | .749 | .673 | .733 |
| Conversion (MeOH) | .689 | .788 | .821 | — | .890 | .736 | .807 | .759 | .681 | .746 |
| Selectivity to Isobutene | .938 | .889 | .916 | — | .789 | .968 | .950 | .972 | .981 | .967 |
| Selectivity to TBA | .001 | .001 | .001 | — | .006 | .001 | .005 | .001 | .001 | .001 |
| Selectivity to Octenes | .045 | .094 | .076 | — | .169 | .030 | .043 | .027 | .017 | .031 |
| Selectivity to Dodecenes | .016 | .016 | .007 | — | .041 | .001 | .006 | .001 | .001 | .001 |
| Selectivity to Dimethylether | .003 | .006 | .005 | — | .012 | .002 | .003 | .002 | .001 | .002 |
| Selectivity to Methanol | .843 | .960 | 1.106 | — | .707 | 1.048 | 1.144 | 1.056 | 1.034 | 1.068 |
| Selectivity to Water | .001 | .002 | .002 | — | .005 | .000 | .001 | .000 | .000 | .000 |
| STY = LHSV × S × C × 100 | 475 | 494 | 516 | — | 507 | 703 | 744 | 855 | 941 | 1010 |

| | EXAMPLE | | | | | | | | |
|---|---|---|---|---|---|---|---|---|---|
| | 11 | 12 | 13 | 14 | 15 | 16 | 17 | 18 | 19 |
| Methyl Ether, Wt. % | .023 | .015 | .009 | .009 | .010 | .013 | .014 | .019 | .023 |
| Isobutylene, Wt. % | 41.85 | 38.54 | 31.93 | 34.11 | 39.57 | 37.44 | 38.19 | 41.82 | 43.24 |
| MTBE, Wt. % | 31.67 | 37.22 | 47.04 | 45.12 | 43.88 | 41.09 | 38.69 | 32.80 | 31.92 |
| Methanol, Wt. % | 25.50 | 23.62 | 20.68 | 20.44 | 16.25 | 21.01 | 22.58 | 24.71 | 24.09 |
| TBA, Wt. % | .060 | .050 | .060 | .060 | .055 | .051 | .049 | .051 | .034 |
| Octenes, Wt. % | .854 | .536 | .277 | .277 | .242 | .418 | .487 | .602 | .702 |
| Dodecenes, Wt. % | .048 | .032 | .000 | .000 | .000 | .000 | .000 | .002 | .000 |
| Data Consistency | 1.044 | 1.057 | 1.123 | 1.04 | .714 | .972 | 1.022 | 1.020 | .961 |
| Conversion (isobutene) | .680 | .623 | .519 | .545 | .588 | .592 | .611 | .670 | .684 |
| Conversion (MeOH) | .690 | .636 | .547 | .555 | .505 | .585 | .675 | .675 | .675 |
| Selectivity to Isobutene | .978 | .984 | .990 | .991 | .993 | .988 | .986 | .985 | .983 |

TABLE II-continued

| | | | | | | | | | |
|---|---|---|---|---|---|---|---|---|---|
| Selectivity to TBA | .001 | .001 | .001 | .001 | .001 | .001 | .001 | .001 | .001 |
| Selectivity to Octenes | .020 | .013 | .009 | .008 | .006 | .011 | .0126 | .014 | .016 |
| Selectivity to Dodecenes | .001 | .001 | .001 | .000 | .000 | .000 | .000 | .000 | .000 |
| Selectivity to Dimethylether | .001 | .001 | .001 | .001 | .001 | .001 | .001 | .001 | .001 |
| Selectivity to Methanol | 1.043 | 1.057 | 1.122 | 1.039 | .714 | .971 | .959 | 1.019 | .959 |
| Selectivity to Water | .000 | .000 | .000 | .000 | .000 | .000 | .000 | .000 | .000 |
| STY = LHSV × S × C × 100 | 947 | 1129 | 1027 | 1080 | 1168 | 1169 | 1206 | 1320 | 1345 |

TABLE III

| | RUN NO. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| LHSV | 2 | 2 | 12.0 | 12.0 | 12.0 | 12.0 | 12.0 | 14.0 | 14.0 | 14.0 | 14.0 | 20.8 | 20.0 | 20.0 |
| Preheater Inlet °C. (Vapor) | 121 | 120 | 129 | 134 | 131 | 142 | 139 | 118 | 122 | 139 | 130 | 146 | 142 | 142 |
| Bath In (Reactor) °C. | 97 | 107 | 133 | 140 | 133 | 139 | 140 | 142 | 137 | 136 | 143 | 142 | 144 | 142 |
| Inlet/Exit Pressure (PSIG) | 0.05/0 | 0.05/0 | 57/40 | 75/73 | 38/21 | 17/0 | 18/0 | 104/99 | 70/62 | 20/0 | 20/0 | 19/0 | 22/0 | 22/0 |
| Reactor Profile (Inches) | | | | | | | | | | | | | | |
| 0 | 90 | 97 | 116 | 122 | 115 | 119 | 116 | 128 | 116 | 120 | 118 | 113 | 125 | 124 |
| 14 | 73 | 80 | 85 | 94 | 77 | 81 | 72 | 98 | 104 | 82 | 77 | 73 | 73 | 73 |
| 30(Bottom) | 92 | 103 | 105 | 111 | 103 | 112 | 99 | 100 | 117 | 107 | 90 | 95 | 94 | 94 |
| % C MTBE | 67.3 | 80.9 | 59.3 | 59.9 | 65.0 | 75.6 | 79.2 | 38.1 | 57.5 | 71.2 | 76.4 | 65.9 | 62.7 | 62.9 |

TABLE IV

| | RUN NO. | | | | | | |
|---|---|---|---|---|---|---|---|
| | 1 | 2 | 3 | 4 | 5 | 6 | 7 |
| Inlet/Exit Pressure, psig | 0.05/0 | 0.05/0 | 57/40 | 75/73 | 38/21 | 17/0 | 18/0 |
| LHSV | 2 | 2 | 12 | 12 | 12 | 12 | 12 |
| Bath In.(Reactor) °C. | 121 | 120 | 129 | 134 | 131 | 142 | 139 |
| Methyl Ether, Wt. % | .14 | .39 | .011 | .06 | .08 | .04 | .16 |
| Isobutene, Wt. % | 37.5 | 38.8 | 37.3 | 99.7 | 41.6 | 44.5 | 37.1 |
| MTBE, Wt. % | 32.7 | 19.1 | 40.7 | 20.8 | 35.1 | 24.4 | 40.1 |
| Methanol, Wt. % | 24.6 | 25.4 | 20.2 | 27.1 | 21.7 | 29.9 | 20.1 |
| TBA, Wt. % | .13 | .14 | .16 | .04 | .12 | .05 | .22 |
| Octenes, Wt. % | 4.51 | 12.6 | 1.53 | 2.28 | 1.48 | 1.07 | 2.37 |
| Dodecenes, Wt. % | .40 | 3.62 | .06 | .17 | .04 | .04 | .03 |
| Data Consistency | 1.023 | .823 | .913 | .913 | .884 | 1.121 | .899 |
| Conversion (i C = /4) | .671 | .819 | .601 | .798 | .659 | .751 | .608 |
| Conversion (MeOH) | .676 | .789 | .579 | .782 | .631 | .772 | .582 |
| Selectivity to Isobutene | .882 | .704 | .956 | .953 | .963 | .951 | .940 |
| Selectivity to TBA | .002 | .002 | .003 | .001 | .002 | .001 | .004 |
| Selectivity to Octenes | .106 | .229 | .039 | .043 | .034 | .048 | .057 |
| Selectivity to Dodecenes | .009 | .007 | .002 | .003 | .001 | .001 | .000 |
| Selectivity to Methyl Ether | .008 | .017 | .007 | .003 | .005 | .002 | .010 |
| Selectivity to Methanol | 1.0145 | .805 | .906 | .910 | .879 | 1.12 | .879 |
| Selectivity to Water | .007 | .007 | .000 | .001 | .000 | .006 | .001 |
| STY - LHSV × S × % C | 118 | 115 | 507 | 912 | 762 | 856 | 684 |

| | RUN NO. | | | | | | |
|---|---|---|---|---|---|---|---|
| | 8 | 9 | 10 | 11 | 12 | 13 | 14 |
| Inlet/Exit Pressure, psig | 104/99 | 70/62 | 20/0 | 20/0 | 19/0 | 22/0 | 22/0 |
| LHSV | 14 | 14 | 14 | 14 | 20.8 | 20 | 20 |
| Bath In. (Reactor) °C. | 118 | 122 | 139 | 130 | 146 | 142 | 142 |
| Methyl Ether, Wt. % | .109 | .09 | .21 | .03 | .393 | .021 | .019 |
| Isobutene, Wt. % | 23.4 | 34.4 | 43.7 | 47.7 | 38.8 | 41.7 | 39.0 |
| MTBE, Wt. % | 61.9 | 42.5 | 28.8 | 23.6 | 19.1 | 37.4 | 37.1 |
| Methanol, Wt. % | 11.7 | 21.7 | 26.8 | 27.6 | 25.4 | 20.3 | 23.4 |
| TBA, Wt. % | .44 | .19 | .06 | .04 | .14 | .05 | .05 |
| Octenes, Wt. % | 2.5 | 1.13 | .59 | 1.030 | 12.6 | .58 | .42 |
| Dodecenes, Wt. % | .02 | 0 | 0 | .02 | 3.62 | .070 | 0 |
| Data Consistency | .791 | 1.07 | 1.061 | .992 | .883 | .839 | 1.038 |

TABLE IV-continued

| | | | | | | | |
|---|---|---|---|---|---|---|---|
| Conversion (i C = /4) | .399 | .569 | .707 | .764 | .819 | .641 | .626 |
| Conversion (MeOH) | .344 | .586 | .720 | .763 | .789 | .599 | .635 |
| Selectivity to Isobutene | .891 | .964 | .986 | .978 | .704 | .984 | .988 |
| Selectivity to TBA | .012 | .004 | .001 | .001 | .002 | .001 | .009 |
| Selectivity to Octenes | .095 | .032 | .013 | .021 | .229 | .014 | .011 |
| Selectivity to Dodecenes | .001 | 0 | 0 | .000 | .066 | .002 | 0 |
| Selectivity to Methyl Ether | .010 | .006 | .001 | .021 | .017 | .001 | .001 |
| Selectivity to Methanol | .781 | 1.064 | 1.060 | .000 | .838 | 1.038 | 1.038 |
| Selectivity to Water | wet feed | wet feed | wet feed | .000 | .000 | .000 | .000 |
| STY - LHSV × S × % C | 498 | 769 | 976 | 1046 | 1199 | 1261 | 1237 |

The invention claimed is:

1. A process for producing high purity isobutene by the dissociation of MTBE comprising contacting a stream in vapor phase and containing MTBE with a microreticular acid cation exchange resin in a fixed bed, the inlet temperature of the vapor phase being in the range of 110° C. to 150° C. and the temperature in said fixed bed being in the range of 90° C. to 160° C., said stream having an LHSV in the range of 7 to 35, thereby dissociating a portion of said MTBE into methanol and isobutene.

2. The process according to claim 1 wherein the inlet temperature of the vapor phase is in the range of 115° C. to 145° C. and the temperature of the fixed bed being in the range of 120° C. to 150° C.

3. The process according to claim 2 wherein the LHSV is in the range of 14 to 25.

4. The process according to claim 1 wherein the MTBE comprises at least 95% wt. of said stream.

5. The process according to claim 4 wherein the MTBE comprises at least 97 wt. % of said stream.

6. The process according to claim 1 wherein said acid cation exchange resin is thermally stabilized.

7. The process according to claim 6 wherein chlorine or bromine groups are incorporated into the resin.

8. The process according to claim 7 wherein chlorine groups are incorporated into the resin.

9. The process according to claim 1 wherein said fixed bed is positioned in a tubular reactor comprising a plurality of tubes containing said acid cation exchange resin, said tubes being mounted in a shell for contact with a heat exchange medium therein.

10. The process according to claim 9 wherein the heat exchange medium supplies heat to the reactor whereby the heat supplied by said heat exchange medium and the vaporized stream containing MTBE maintain the temperature in said fixed bed.

11. The process according to claim 1, wherein there is a pressure drop through said fixed bed in the range of 0.5 to 50 psig at reaction pressure in the range of 0.5 to 4 atmospheres.

12. A process for producing high purity isobutene from a C$_4$ hydrocarbon stream containing isobutene comprising contacting said C$_4$ hydrocarbon stream and methanol in liquid phase with a macroreticular acid cation exchange resin in a first fixed bed reactor, reacting said isobutene and methanol preferentially to produce MTBE, removing a product stream containing MTBE from the reactor, recovering an MTBE stream from said product stream, feeding a portion of said MTBE stream in vapor phase at an inlet temperature in the range of 110° C. to 150° C. to a second fixed bed reactor containing a macroreticular acid cation exchange resin, the temperature in said fixed bed being in the range of 90° C. to 160° C., said MTBE stream having an LHSV in the range of 7 to 35, dissociating a portion of said MTBE into methanol and isobutene, and recycling the undissociated MTBE to said first reactor.

13. The process according to claim 12 wherein the inlet temperature of said MTBE stream is in the range of 115° C. to 145° C. and the temperature in said fixed bed is in the range of 120° C. to 150° C.

14. The process according to claim 13 wherein the LHSV is in the range of 14 to 25.

15. The process according to claim 12 wherein said second fixed bed reactor is a tubular reactor comprising a plurality of tubes containing said acid cation exchange resin and mounted in a shell and surrounded therein by a heat exchange medium for supplying heat to said fixed bed whereby said heat exchange medium and said vaporized MTBE stream maintain the temperature of said fixed bed.

16. The process according to claim 12 wherein said MTBE stream comprises at least 95 wt. % MTBE.

17. The process according to claim 16 wherein said MTBE stream comprises at least 97 wt. % MTBE.

18. The process according to claim 12 wherein said acid cation exchange resin is thermally stabilized.

19. The process according to claim 18 wherein said acid cation exchange resin has electron withdrawing groups incorporated therein.

20. The process according to claim 19 wherein chlorine or bromine groups are incorporated into the resin.

21. The process according to claim 20 wherein chlorine groups are incorporated into the resin.

22. A process for producing high purity isobutene by the dissociation of MTBE comprising contacting a stream in vapor phase and containing at least 95% wt. MTBE with a microreticular acid cation exchange resin in a fixed bed, the inlet temperature of the vapor phase being in the range of 115° C. to 145° C. and the temperature in said fixed bed being in the range of 120° C. to 150° C., said stream having an LHSV in the range of 14 to 25, thereby dissociating a portion of said MTBE into methanol and isobutene.

* * * * *

UNITED STATES PATENT OFFICE
CERTIFICATE OF CORRECTION

PATENT NO. : 4,570,026
DATED : February 11, 1986
INVENTOR(S) : D. A. Keyworth and C. G. McFarland It is certified that error appears in the above-identified patent and that said Letters Patent are hereby corrected as shown below:

Col. 1, Line 16 reads "dissociation alkyltertiary" but should read --- dissociation of alkyltertiary ---

Col. 7, Line 26 reads "being isobutene" but should read --- being isobutane ---

Col. 7, Line 67 reads "The wsh" but should read --- The wash ---

Col 9, TABLE I captions at left read "Reactor Profile" but should read --- Reactor Profile °C ---

Col. 11, TABLE III, captions at left read "Reactor Profile" but should read --- Reactor Profile °C ---

Col. 13, TABLE IV, captions at left read "conversion (i C = /4)" but should read --- conversion (isobutene) ---

Signed and Sealed this

Twenty-fourth Day of March, 1987

Attest:

DONALD J. QUIGG

Attesting Officer   Commissioner of Patents and Trademarks